United States Patent
Xu et al.

(10) Patent No.: US 7,812,188 B2
(45) Date of Patent: Oct. 12, 2010

(54) PREPARATION OF ADSORBENTS FOR PURIFYING ORGANOSILICON COMPOUNDS

(75) Inventors: Mindi Xu, Naperville, IL (US); Trapti Chaubey, Wilmington, DE (US)

(73) Assignee: American Air Liquide, Inc., Fremont, CA (US)

( * ) Notice: Subject to any disclaimer, the term of this patent is extended or adjusted under 35 U.S.C. 154(b) by 298 days.

(21) Appl. No.: 11/608,096

(22) Filed: Dec. 7, 2006

(65) Prior Publication Data

US 2008/0009645 A1     Jan. 10, 2008

Related U.S. Application Data

(60) Provisional application No. 60/748,185, filed on Dec. 7, 2005.

(51) Int. Cl.
*C07F 7/04* (2006.01)
(52) U.S. Cl. ............... 556/440; 556/451; 556/470; 556/483
(58) Field of Classification Search ............ 556/440, 556/451, 470, 483
See application file for complete search history.

(56) References Cited

U.S. PATENT DOCUMENTS

| 6,393,527 | B1 | 5/2002 | Rao et al. | |
|---|---|---|---|---|
| 6,797,036 | B2 | 9/2004 | Funke et al. | |
| 6,852,299 | B2 | 2/2005 | Kohmura et al. | |
| 6,852,399 | B2 | 2/2005 | Takahashi et al. | |
| 6,878,657 | B2 * | 4/2005 | Jasra et al. | 502/64 |
| 6,890,373 | B2 * | 5/2005 | Nemoto et al. | 95/90 |
| 6,892,473 | B1 | 5/2005 | Chiang et al. | |
| 6,939,527 | B2 | 9/2005 | Oeter et al. | |
| 7,108,771 | B2 * | 9/2006 | Xu et al. | 203/41 |
| 7,365,220 | B2 * | 4/2008 | Lewis et al. | 556/482 |
| 2004/0038803 | A1 | 2/2004 | Zhou et al. | |
| 2005/0054211 | A1 * | 3/2005 | Xu et al. | 438/745 |

* cited by examiner

*Primary Examiner*—Daniel M Sullivan
*Assistant Examiner*—Chukwuma O Nwaonicha
(74) *Attorney, Agent, or Firm*—Patricia E. McQueeney

(57) ABSTRACT

A method for purifying organosilicon precursor compounds is provided. It includes preparation of the adsorbent with a treating compound. The thus-treated adsorbents can be used to remove impurities such as organic impurities and moisture from a composition containing an organosilicon containing compound. In this manner, it is able to purify organosilicon precursors (or solutions containing organosilicon precursors) without inducing decomposition of the organosilicon precursor.

15 Claims, 10 Drawing Sheets

PREPARATION OF ADSORBENTS FOR PURIFYING ORGANOSILICON COMPOUNDS

CROSS-REFERENCE TO RELATED APPLICATIONS

This application claims the benefit under 35 U.S.C. § 119(e) to provisional application No. 60/748,185, filed Dec. 7, 2005, the entire contents of which are incorporated herein by reference.

BACKGROUND

Precursor chemicals for semiconductor manufacturing process must be purified to meet the needs for depositing high quality films. Moisture and organic species are the impurities commonly found in the precursor chemicals. The traditional distillation can separate the impurities from the precursor chemicals. However, this method is too expensive and requires a sophisticated system. In addition, some of the precursor chemicals may be heat sensitive and decompose at high temperature so that the distillation method is limited in the application. Another traditional method is to use adsorbents to remove trace impurities in the precursor chemicals. Tests have found that some of the precursor chemicals are not compatible with adsorbents including activated carbons, molecular sieves, and other synthetic adsorbents. For example, dimethyldimethoxysilane as a low-k precursor exhibits some decomposition after contacting with the mentioned adsorbents, resulting in the formation of impurities.

U.S. Pat. No. 6,878,657 discloses the use of liquid phase alkoxide to deposit on the surface of zeolite NaA to change the pore size for selectivity. This method is useful to modify the specific adsorbent for more precise mouth opening of the pores and, therefore, gas species having close sizes would be separated. However, the surface modified zeolite still does not address decomposition of the precursor materials because the precursor materials may still decompose after contact with the adsorbent.

U.S. Pat. No. 6,890,373 discloses a method to prepare adsorbent that will not shed particles under pressure. The adsorbent was prepared by depositing metal compound and water soluble polymer on a core particle of adsorbing material and then coating it with polymer material. This type of adsorbent has the potential of preventing the direct contact of adsorbing materials with the fluid to be purified. It also potentially increases the transport distance of impurities from the fluid into adsorbing material. It, too, does not address decomposition of organosilicon precursors due to the contact of organosilicon precursors and adsorbent.

U.S. Published Patent Application 2004/0038803 discloses a method to treat adsorbents by heating them to different temperatures under an inert gas purge, and then passivating the adsorbents by flowing corrosive gas through the adsorbent.

Others have proposed some solutions, including U.S. Pat. Nos. 6,852,299, 6,939,527, 6,797,036, and 6,892,473.

SUMMARY

A method for purifying organosilicon precursor compounds is provided. It includes preparation of the adsorbent with a treating compound. The thus-treated adsorbents can be used to remove impurities such as organic impurities and moisture from a composition containing an organosilicon containing compound. In this manner, it is able to purify organosilicon precursors (or solutions containing organosilicon precursors) without inducing decomposition of the organosilicon precursor.

DESCRIPTION OF PREFERRED EMBODIMENTS

Figure 1:
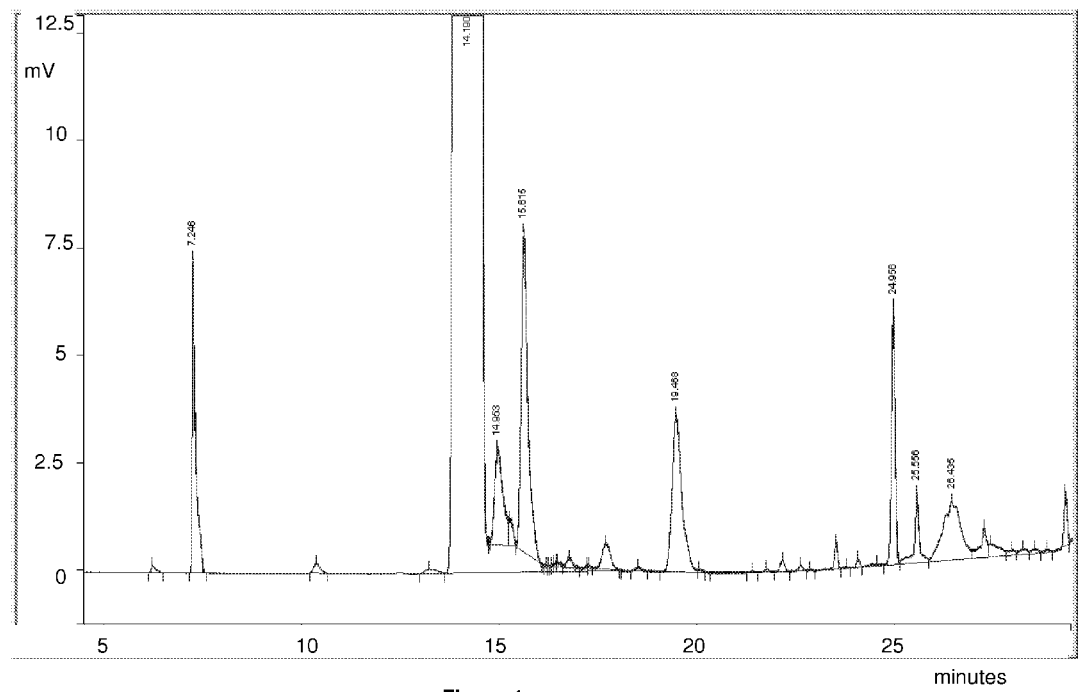
FIG. 1 is a chromatogram of unpurified DMDMOS

We provide a method for purifying organosilicon precursor compounds. It includes preparation of the adsorbent with a treating compound. The thus-treated adsorbents can be used to remove impurities such as organic impurities (for example, methanol) and moisture from a composition containing an organosilicon containing compound. In this manner, it is able to purify organosilicon precursors (or solutions containing organosilicon precursors) without inducing decomposition of the organosilicon precursor.

The organosilicon compound intended to be purified can be present in solution or without a solvent. Organosilicon compounds suitable for purification include those according to formulae I-V:

(I) $SiR^1R^2R^3R^4$, wherein each of the $R^1$-$R^4$ is independently either H, $CH_3(CH_2)_n$, or $CH_3(CH_2)_nO$, at least one of the $R^1$-$R^4$ is $CH_3(CH_2)_nO$, and n is independently 0 or 1

(II) $SiR^1R^2R^3$—$SiR^4R^5R^6$, wherein each of the $R^1$-$R^6$ is independently either H, $CH_3(CH_2)_n$, or $CH_3(CH_2)_nO$, at least one of the $R^1$-$R^6$ is $CH_3(CH_2)_nO$, and n is independently 0 or 1

(III) $SiR^1R^2R^3$—O—$SiR^4R^5R^6$, wherein each of the $R^1$-$R^6$ is independently either H, $CH_3(CH_2)_n$, or $CH_3(CH_2)_nO$, and n is independently 0 or 1

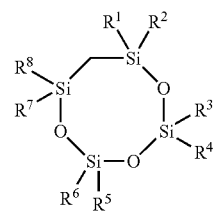

(IV)

wherein each of the $R^1$-$R^8$ is independently either H, $CH_3(CH_2)_n$, or $[OCH_3(CH_2)_n]_mSiH_p$; n=0-1; m=1-4; p=0-3; and m+p=4

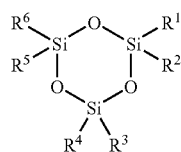

(V)

wherein each of the $R^1$-$R^6$ is independently either H, $CH_3(CH_2)_n$, or $[OCH_3(CH_2)_n]_m SiH_p$; n=0-1; m=1-4; p=0-3; and m+p=4.

Particularly preferred organosilicon compounds include dimethyldimethoxysilane (DMDMOS), tetramethylcyclotetrasiloxane (TMCTS), tetramethylorthosilicate (TMOS), and tetraethylorthosilicate (TEOS).

One or more adsorbent materials can be selected for use within an adsorption unit to facilitate effective adsorption of impurities such as organic compounds (for example, methanol) and/or moisture from the organosilicon material. Typical adsorbents include, without limitation, activated carbon materials, zeolites, and synthetic adsorbents. Particularly suitable adsorbents include activated carbon, hydrophobic polymeric resin adsorbents, Ambersorb 563 available from Rohm & Haas Co., and Ambersorb 348-F available from Sigma Aldrich website, molecular sieve 4 Å, molecular sieve 5 Å or molecular sieve 13X. These adsorbent materials are in the form of beads that can be mixed and installed in a single adsorption unit for removing organic impurities and moisture.

The adsorption unit can be constructed of any suitable materials including, without limitation, stainless steel, plastics, quartz, glass, and other metals. In particular, it is noted that the construction materials for the adsorption unit are preferably compatible with the chemical compounds making up the material to be purified and further minimize or prevent the leaching of impurities into the processed material. The adsorption unit can further have a cylindrical, rectangular or any other suitable shape and is suitably dimensioned to provide a sufficient volume capacity to hold a sufficient amount of adsorbent material within the bed. It is understood that the dimensions of the adsorption unit will depend upon the flow rate and impurity concentrations of the low-k silicon containing material to be processed within the adsorption unit. For example, the adsorption unit can be cylindrical, with a length of about at least about 15 centimeters (about 6 inches) and a diameter of at least about 0.635 centimeter (about 0.25 inch). Preferably, the adsorption unit has a length of at least about 30.5 centimeters (about 12 inches) and a diameter of at least about 2.54 centimeters (about 1 inch). Providing an adsorption unit with the dimensions as described above will facilitate effective processing of raw material at flow rates of at least about 10 milliliters per minute.

Suitable types of treatment compounds include those according to formula VI:

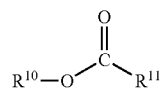

(VI)

wherein each of $R^{11}$ and $R^{12}$ are independently selected from hydrogen, alkyls, alkenyls, ketones, alcohols, ethers, silanes, silanols, and siloxanes. Typically it is not reactive with the compound to be purified and/or it is used at a temperature at which it is a liquid or a solid that can be dissolved at that temperature, and/or it does not form a solid polymer during performance of the invention. Preferred treatment compounds include 3-methacryloxypropyltrimethoxysilane (MPTMS) and tetramethylcyclotetrasiloxane (TMCTS).

Without being bound by any one theory, we believe the following can occur during processing of the organosilicon compounds. Certain undesired impurities present in the organosilicon-containing composition can catalyze the organosilicon compound by attacking the Si—O bond thereby decomposing the compound. We believe that the treatment compound either preferentially chemisorbs the catalyst or preferentially reacts with the catalyst, thereby reducing the risk of decomposition of the organosilicon compound. We also believe that the electronegative character of the oxygen in the O—C=O linkage of the treatment compound provides a site for chemisorption of the catalyst or a reactive site for reaction with the catalyst.

The method can include any one or more of the following aspects:

the treating compound is either a liquid or a solid dissolved in a solvent.
the treating compound is not reactive with the organosilicon compound.
the treating compound does not form a solid polymer during exposure of the adsorbent to the treating compound.
the organosilicon compound is dimethyldimethoxysilane
the organosilicon compound is tetramethylorthosilicate.
the organosilicon compound is tetraethylorthosilicate.
the organosilicon compound is tetramethylcyclotetrasiloxane (TMCTS).
the treatment compound is 3-methacryloxypropyltrimethoxysilane.
the treatment compound is tetramethylcyclotetrasiloxane.

In performance of the method, the adsorbent is typically dried. While each of the following is not essential, the drying may be performed at about 100 to about 400° C. for about 1 to about 24 hours under vacuum or at about 100° C. to about 400° C. for about 1 to about 24 hours while purging with Nitrogen. A preferred drying temperature is about 200 to about 350° C. A preferred drying time is about 8 to about 24 hours while an especially suitable drying time is about 8 to about 10 hours. Typically, the dried adsorbent is then purged with nitrogen to remove any contaminants adsorbed thereupon.

After this initial treatment, the adsorbent is exposed to the treating compound for a period of time. While any particular soak time is not essential, the adsorbent is typically allowed to soak in the treating compound for about 1 to about 48 hours. A preferred soaking time is about 8 to about 48 hours. While also not essential to the method, the treating compound-exposed adsorbent is typically purged with an inert gas, such as nitrogen or helium, at a temperature above the boiling point of the treating compound. While also not essential to the method, this is typically done for about 0.5 to about 24 hours. A preferred purge time is from about 8 to about 10 hours. A more preferred purge time is from about 6 to about 12 hours.

The composition containing the organosilicon compound is then introduced into an inlet of the adsorptive unit for purification thereby. The adsorption unit can be configured to receive organosilicon-containing raw materials from a suitable supply source (e.g., storage containers), where the materials are delivered with a pump or through pressurization with a high pressure inert gas, such as helium or nitrogen, to the adsorption unit. The purified composition is then withdrawn from the outlet. While this can be performed batch-wise, it is preferably performed continuously.

Typically, the adsorptive unit is regenerated periodically in order to enhance performance. As an example, they may be regenerated by purging with an inert gas such as Nitrogen at a temperature from about 100 to about 400° C. This may be done for a period of time of about 1 to about 24 hours. A preferred regeneration temperature is from about 200 to about 350° C. A preferred regeneration time is from about 8 to about 24 hours.

EXAMPLES

Comparative Example 1

Various adsorbents were initially used to purify DMDMOS: Ambersorb 563, Ambersorb 348F, and molecular sieves 3A, 4A, 5A, 13X. Each of the adsorbents was kept in a clean 1.8 mL glass sample vial. The vials were heated in a vacuum oven to 150° C. for a minimum of 10 hours. They were then transferred to a glove box to cool. Approximately 0.5-1 milliliters of DMDMOS were then added to each vial. Each adsorbent was allowed to soak in the DMDMOS for five minutes, and then a sample was analyzed with a gas chromatograph (GC). All tests were done in a glove box pressurized with nitrogen as to reduce contamination from ambient air at the same operation condition as for DMDVS analysis.

Figure 2:
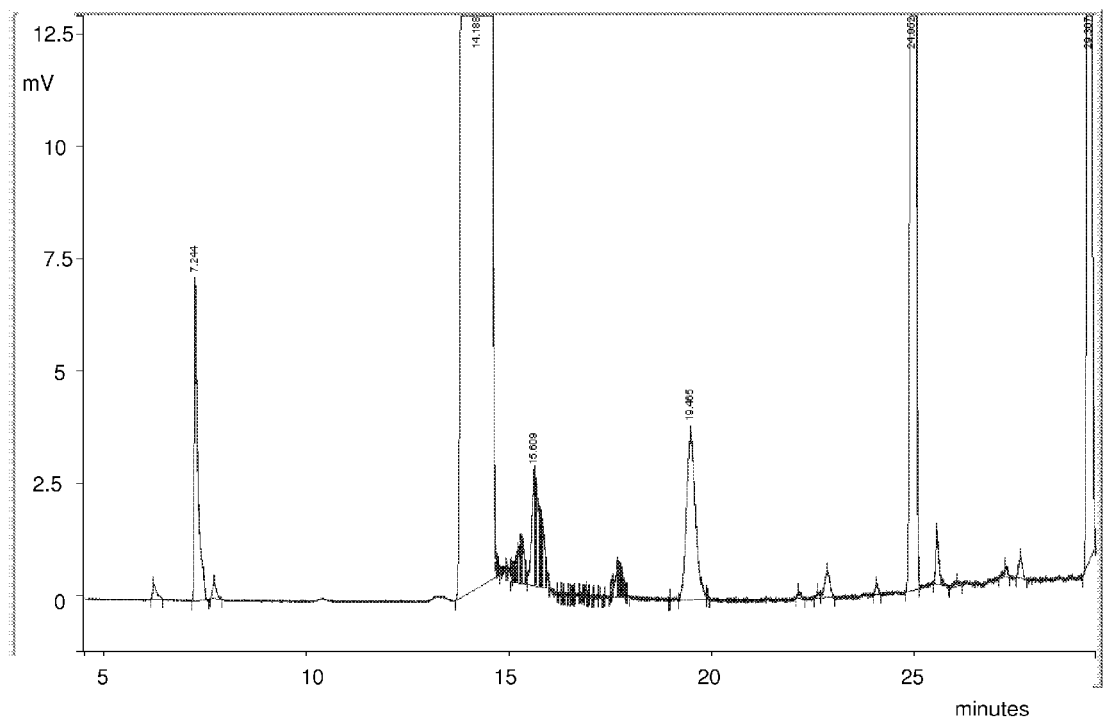
FIG. 2 is a chromatogram of DMDMOS scrubbed with Ambersorb 563.

A chromatogram of the DMDMOS without any adsorbent treatment is shown in FIG. 1. DMDMOS is located at the 14.1 minute, methanol at the 7.2 minute and unknown contaminants are scattered throughout the chromatogram. A chromatogram of the DMDMOS treated with Ambersorb 563 is shown in FIG. 2. FIG. 2 indicates that the methanol concentration was unchanged after treatment by Ambersorb 563, however, the peaks at 24.9 minutes and 29.3 minutes increased drastically. It is suspected that these peaks are DMDMOS decomposition products. Under the same condition, a hydrophilic ion-exchange resin called Ambersorb 348F was tested and shows higher peak height with numerous unknown peaks. At this time, it is uncertain as to the identity of the contaminants. It seems that the two adsorbents do not adequately purify DMDMOS by themselves under these conditions.

Figure 3:
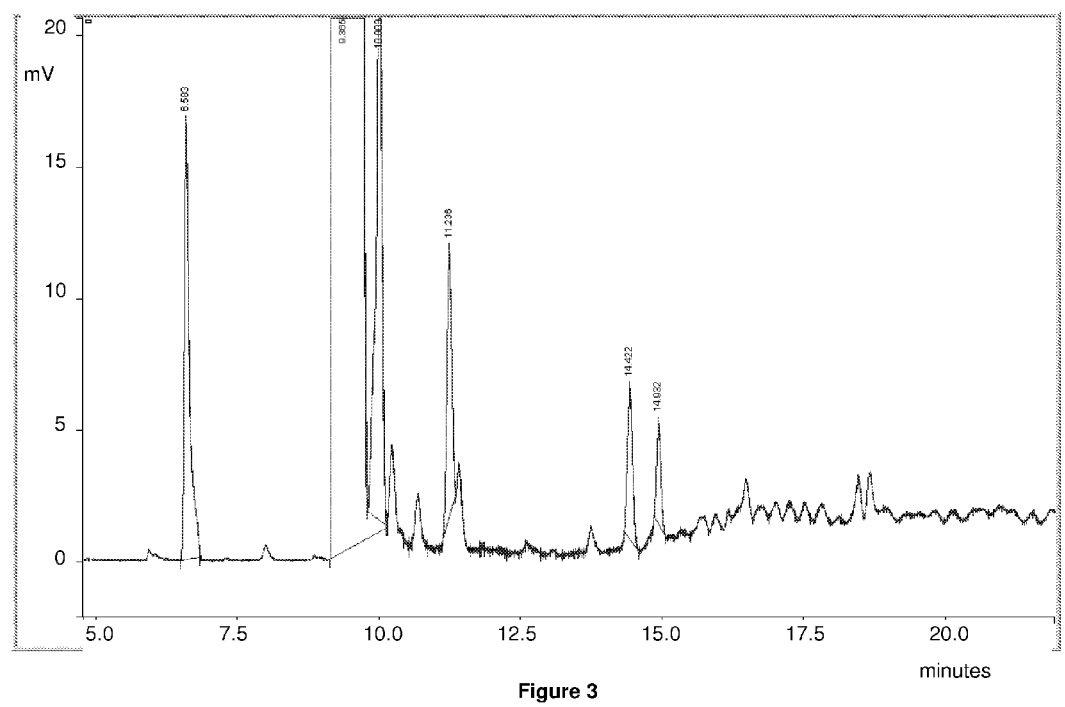
FIG. 3 is a chromatogram of unpurified DMDMOS.
Figure 4:
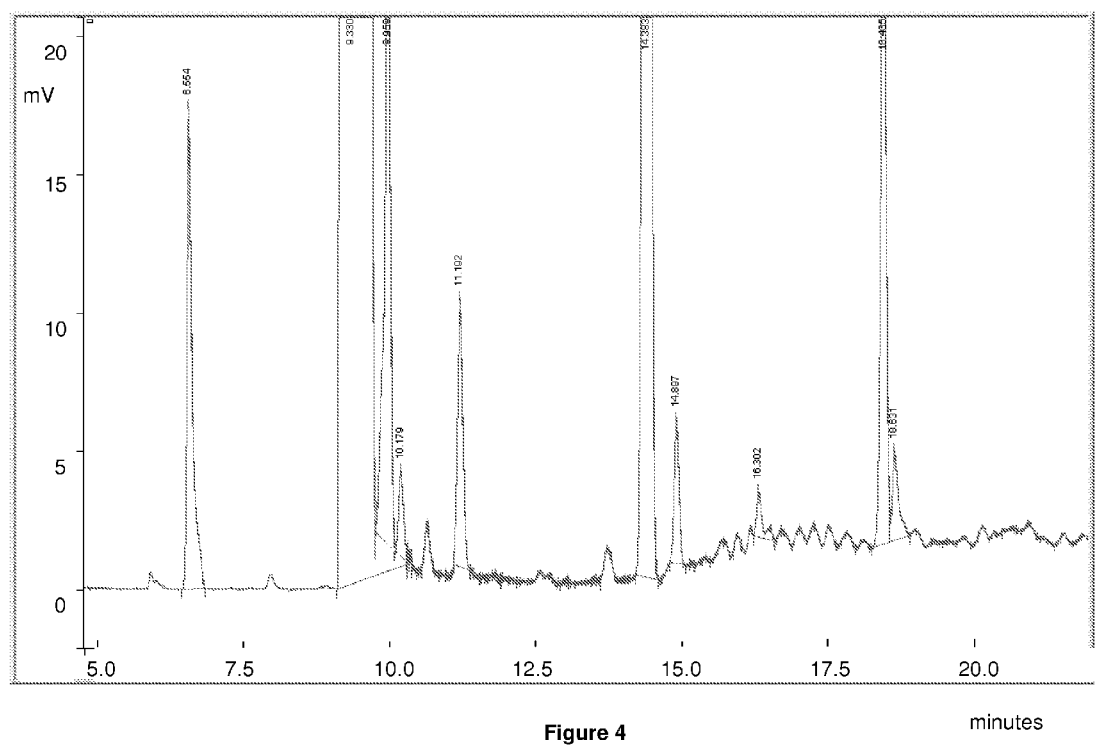
FIG. 4 is a chromatogram of DMDMOS scrubbed with a 3 Å molecular sieve.

Molecular sieves 3A, 4A, 5A, 13X were next tested for their effectiveness in purifying DMDMOS of organic impurities. To reduce the test run time on the GC, a modified method with broader oven temperature range and ramp than the previous method was used. FIG. 3 shows the chromatogram of the untreated DMDMOS under a modified method. Methanol appears at 6.6 minutes while DMDMOS shows up at 9.4 minutes. The remaining major peaks are unknowns. FIG. 4 shows the chromatogram of DMDMOS treated with the 3A molecular sieve. It can be seen that the methanol peak was unaffected by the 3A molecular sieve. On the other hand, other impurity peaks increased significantly.

The results from 4A molecular sieve were very similar. Since some peaks have not been identified, it is unclear as to why this occurred. The other two samples were treated with 5A and 13X respectively. The results were similar to the other mol sieves and only differ in the extent of the height of the unknown peaks.

These comparative example results indicate that Ambersorb 563, Ambersorb 348F, and molecular sieves 3A, 4A, 5A, 13X, by themselves, are not satisfactorily effective in removing methanol and other impurities from DMDMOS. In fact, they enhanced and in some case added impurities.

Comparative Example 2

Figure 5:
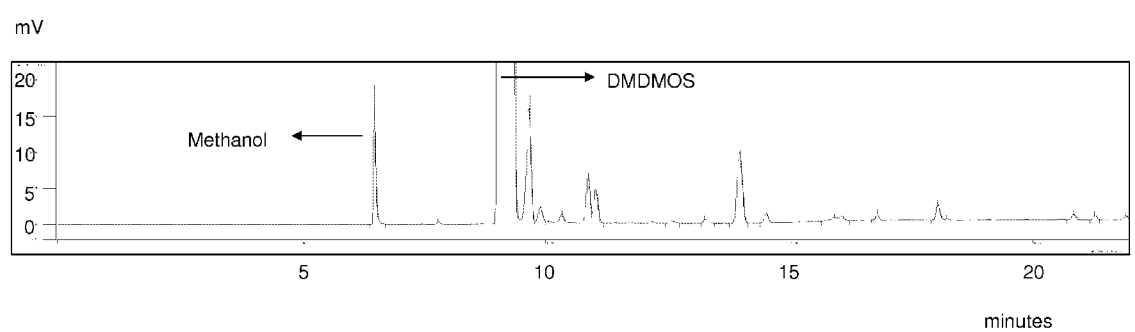
FIG. 5 is a chromatogram of unpurified DMDMOS.

A gas chromatogram of a DMDMOS sample before purification is shown in FIG. 5.

Several adsorbents (activated carbon, ambersorb 563, ambersorb 348f, and molecular sieves 4 Å, 5 Å and 13 X were selected for a screening test. Each of the adsorbents (0.3 gm) was heated in a 2 ml sample vial in a vacuum oven at 140° C. for 8 hours. The adsorbents were then soaked in 3-methacryloxypropyltrimethoxysilane (MPTMS) for 24 hours and dried by purging with nitrogen above the boiling point of the chemical (~200° C.) for 8-10 hours. 1 ml of DMDMOS was added to each of these adsorbents and tested after 24 hours with GC.

Figure 6:
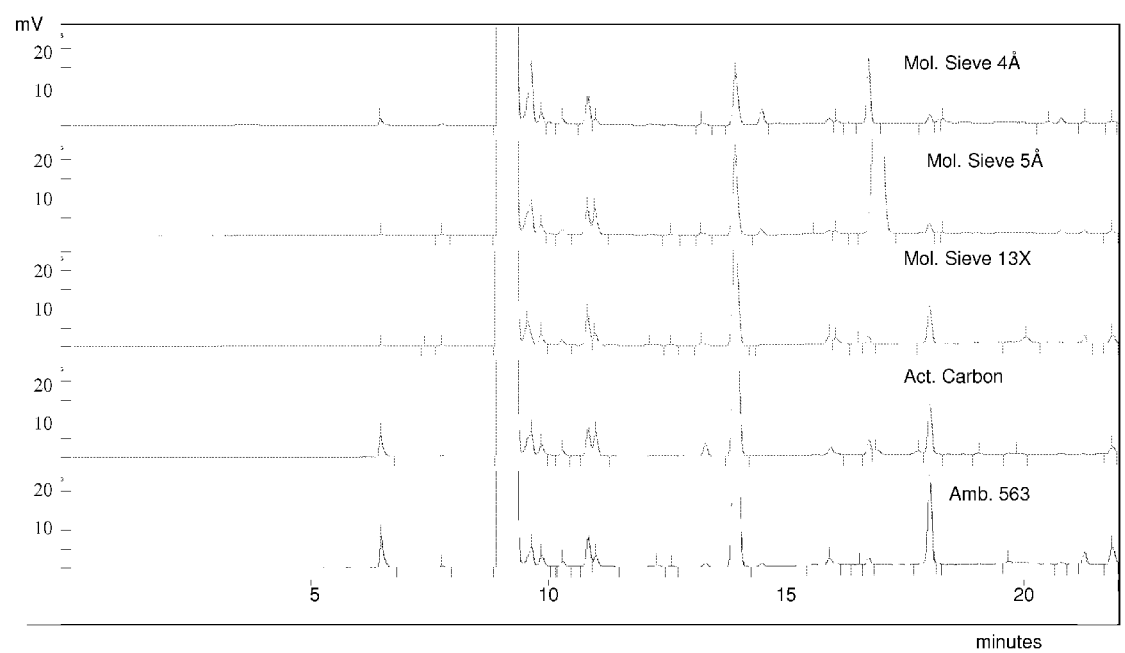
FIG. 6 are chromatograms of DMDMOS purified with molecular sieve 4 Å, molecular sieve 5 Å, molecular sieve 13X, activated carbon, and Ambersorb 563, each of which was treated with MPTMS beforehand.
Figure 7:
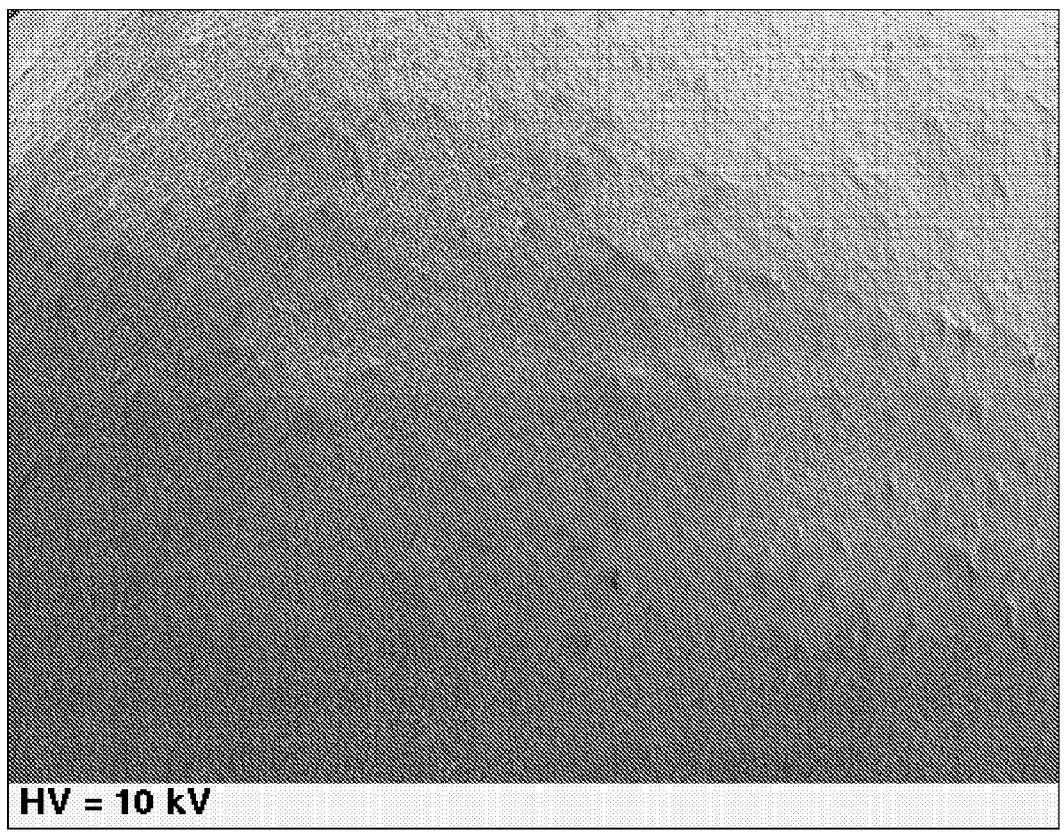
FIG. 7 is scanning electron microscope (SEM) image of the untreated molecular sieve 4 Å at 100× magnification.
Figure 8:
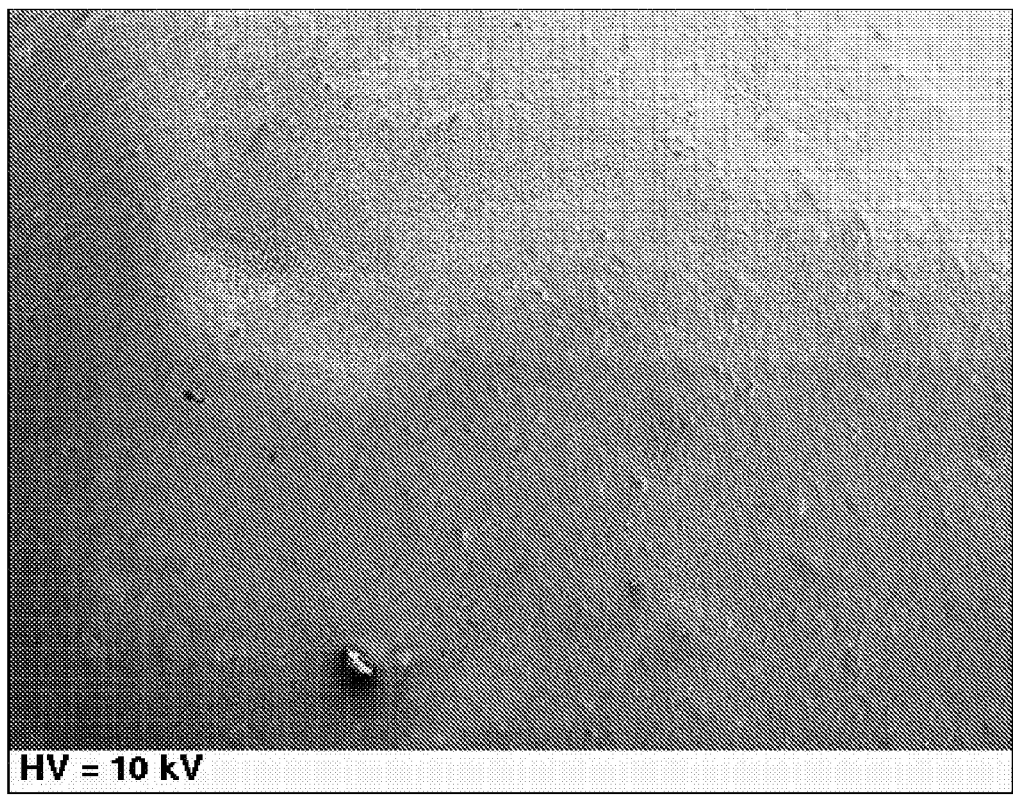
FIG. 8 is scanning electron microscope (SEM) image of molecular sieve 4 Å treated with 3-methacryloxypropyltrimethoxysilane (MPTMS) at 100× magnification.
Figure 9:
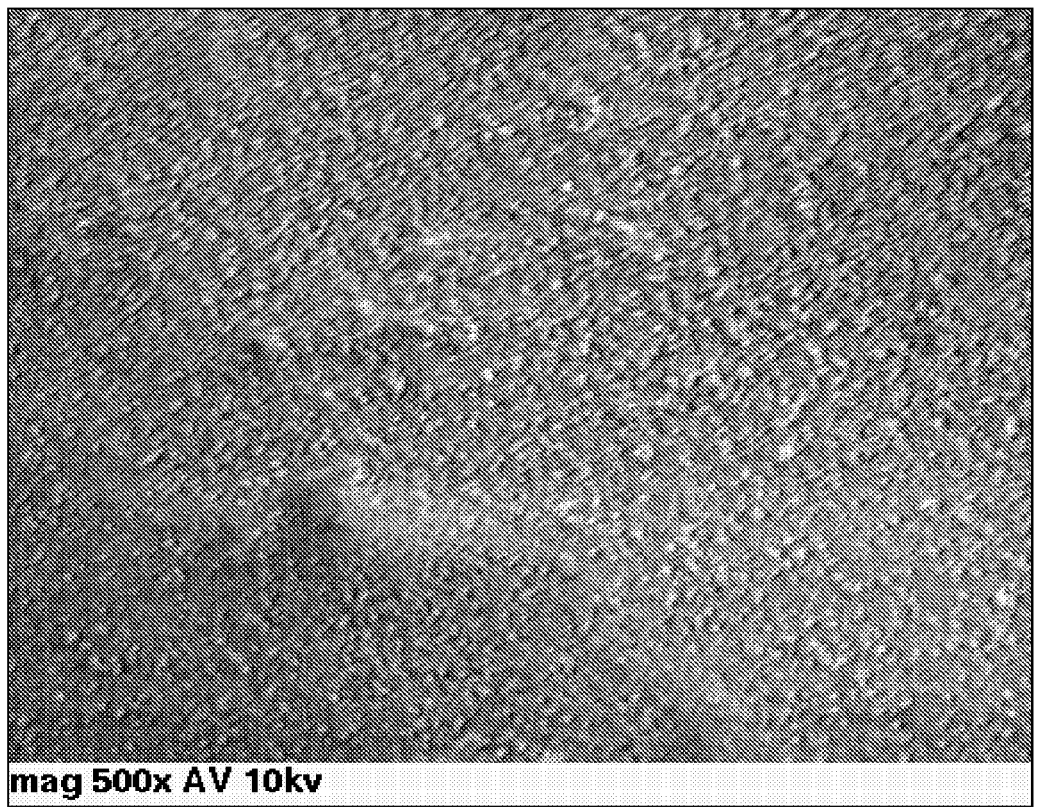
FIG. 9 is scanning electron microscope (SEM) image of the untreated molecular sieve 4 Å at 500× magnification.
Figure 10:
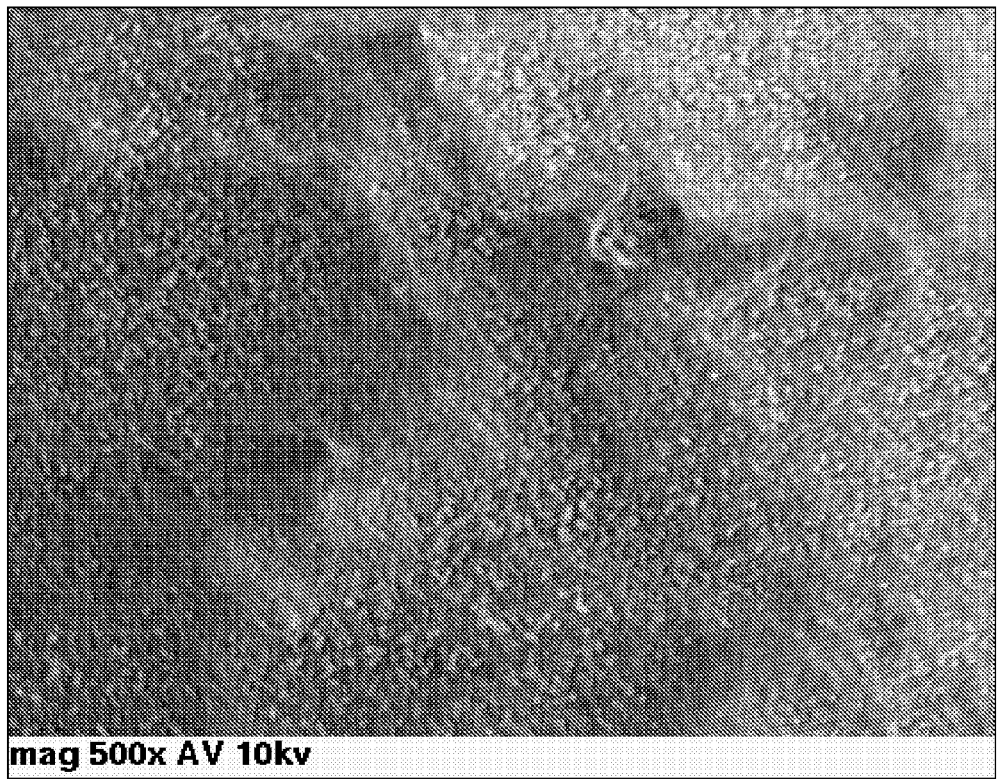
FIG. 10 is scanning electron microscope (SEM) image of molecular sieve 4 Å treated with 3-methacryloxypropyltrimethoxysilane (MPTMS) at 500× magnification.

Chromatograms of the DMDMOS sample after purification with Ambersorb 563, activated carbon, molecular sieve 4 Å, molecular sieve 5 Å and molecular sieve 13X are shown in FIG. 6. They all proved to be effective in removing methanol to some degree. While additional peaks are believed to be the minimal contaminants from the DMDMOS from decomposition, those peaks are not of the same order of magnitude as those exhibited by the chromatograms of FIG. 6. This indicates that treatment of the adsorbents with MPTMS is effective in removing methanol and decreasing the potential amount of DMDMOS degradation.

A purification setup was constructed for continuous purification of DMDMOS. A stainless steel column with 1" O.D, 0.835" I.D and 14.5" long was packed with ~115 gm of molecular sieve 4 Å. There were four adsorbent preparation steps. First, the molecular sieve was heated to a temperature of 200° C. for 8-10 hours. Second, it was purged with nitrogen to remove any contaminants adsorbed on the surface of the molecular sieve. Third, sufficient amount of 3-methacryloxy propyltrimethoxysilane was introduced into the column to allow soaking the adsorbent for 24 hours. Finally, the molecular sieve was dried by heating it to a temperature of 200° C. and purging with nitrogen for 8-10 hours.

After these steps, liquid DMDMOS was forced to flow from a tank at 9.5 ml/min to the column under nitrogen pressure. Samples were collected every 10 to 15 minutes. A bypass line was used to flush the lines.

The molecular sieve was then regenerated by heating it to a temperature of 200° C. for 8-10 hours and used again for the DMDMOS purification to study the regeneration capacity of the molecular sieve. It was found that the regenerated adsorbent performs excellent.

A Metrohm 831 Karl Fisher titrator was used to measure the moisture concentration in treated and untreated DMDMOS samples. The analysis was performed inside the nitrogen purged glove box to avoid any contamination from the environment. Table II gives the sample weights and concentrations of moisture in the samples.

The molecular sieve 4 Å was analyzed using a Scanning Electron Microscope (SEM) for studying the physical and chemical properties before and after treatment with 3-methacryloxypropyltrimethoxysilane (MPTMS). The molecular sieve 4 Å is sodium aluminosilicate with a molecular formula of $Na_2O-Al_2O_3-2SiO_2-nH_2O$. To look for any change in the chemical composition an X-ray diffraction microanalysis was used to quantify the elemental composition of the molecular sieve. The acceleration voltage was 10 kV and the working distance was 14 mm. The images and X-ray were taken at 100× and 500× magnification at 4 different spots.

TABLE II

| Karl Fischer Moisture analysis for DMDMOS | | | | |
|---|---|---|---|---|
| Feed | Sample | Sample wt. (gm) | Conc. of H20 (ppm) | Avg. Moisture conc. (ppm) |
| Batch I | Blank | 1.98371 | 35.84 | 35.34 |
|  |  | 3.90144 | 34.83 |  |
|  | Purified flow rate: 9.5 ml/min | 3.0862 | 13.84 | 13.24 |
|  |  | 5.10905 | 12.53 |  |
|  |  | 5.9784 | 13.35 |  |
|  | Purified flow rate: 3.5 ml/min | 4.45869 | 8.3 | 7.94 |
|  |  | 7.84399 | 8.24 |  |
|  |  | 8.00599 | 7.29 |  |

TABLE II-continued

Karl Fischer Moisture analysis for DMDMOS

| Feed | Sample | Sample wt. (gm) | Conc. of H20 (ppm) | Avg. Moisture conc. (ppm) |
|---|---|---|---|---|
| Batch II | Blank | 6.56714 | 50.81 | 50.64 |
| | | 2.19611 | 51.82 | |
| | Purified flow rate 3.5 ml/min | 3.31642 | 13.27 | 13.45 |
| | | 5.15277 | 13.62 | |

X-ray Diffraction Analysis was performed on 6 different spots. Some small changes in the chemical composition of molecular sieves were observed. As best seen in the SEM images of FIGS. 7-10, it seems as if the surface of the treated molecular sieve was been slightly smoothed.

Some conclusions can be made.

First, it was seen that the molecular sieve 4 Å was relatively more effective in purifying organosilicon such as DMDMOS without inducing decomposition.

Second, 3-methacryloxypropyltrimethoxysilane (MPTMS) and tetramethylcyclotetrasiloxane (TMCTS), were quite useful for treating adsorbents such as molecular sieve 4 Å. Through the purification bed, methanol and water were reduced from 71 ppm and 35 ppm to 25 ppm and 13 ppm respectively at the flow rate of 9.5 ml/min. At a lower flow rate of 3.5 ml/min, the concentrations were reduced from 71 ppm and 35 ppm to 0.75 ppm and 7.9 ppm respectively. The adsorbent bed was regenerated and used for the DMDMOS purification. There were no sign of decomposition and the bed performed efficiently for the purification process.

What is claimed is:

1. A method of purifying organosilicon compounds, comprising:
    A) providing an adsorbent;
    B) exposing the adsorbent to a treating compound selected from the group consisting of 3-methacryloxypropyltrimethoxysilane and tetramethylcyclotetrasiloxane; and
    C) allowing a composition containing at least one organosilicon compound to pass through the exposed adsorbent, wherein the organosilicon compound comprises at least one member selected from the group consisting of:
        i) $SiR^1R^2R^3R^4$, wherein each of the $R^1$-$R^4$ is independently either H, $CH_3(CH_2)_n$, or $CH_3(CH_2)_nO$, at least one of the $R^1$-$R^4$ is $CH_3(CH_2)_nO$, and n is independently 0 or 1,
        ii) $SiR^1R^2R^3$—$SiR^4R^5R^6$, wherein each of the $R^1$-$R^6$ is independently either H, $CH_3(CH_2)_n$, or $CH_3(CH_2)_nO$, at least one of the $R^1$-$R^6$ is $CH_3(CH_2)_nO$, and n is independently 0 or 1,
        iii) $SiR^1R^2R^3$—O—$SiR^4R^5R^6$, wherein each of the $R^1$-$R^6$ is independently either H, $CH_3(CH_2)_n$, or $CH_3(CH_2)_nO$, and n is independently 0 or 1,

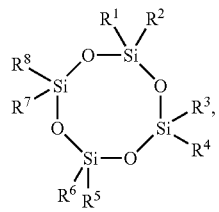

(iv)

wherein each of the $R^1$-$R^8$ is independently either H, $CH_3(CH_2)_n$, or $[OCH_3(CH_2)_n]_mSiH_p$, n=0-1, m=1-4, p=0-3, and m+p=4, and

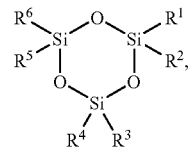

(v)

wherein each of the $R^1$-$R^6$ is independently either H, $CH_3(CH_2)_n$, or $[OCH_3(CH_2)_n]_mSiH_p$, n=0-1, m=1-4, p=0-3, and m p=4.

2. The method of claim 1, wherein the treating compound in contact with the adsorbent being either a liquid or a solid dissolved in a solvent.

3. The method of claim 1, wherein the treating compound is not reactive with the organosilicon compound.

4. The method of claim 1, wherein the treating compound does not form a solid polymer during said step of exposing the adsorbent to a treating compound.

5. The method of claim 1, wherein the organosilicon compound is dimethyldimethoxysilane.

6. The method of claim 1, wherein the treating compound is tetramethylcyclotetrasiloxane.

7. The method of claim 1, wherein the organosilicon compound is tetramethylorthosilicate.

8. The method of claim 1, wherein the organosilicon compound is tetraethylorthosilicate.

9. The method of claim 5, wherein the treatment compound is 3-methacryloxypropyltrimethoxysilane.

10. The method of claim 1, wherein the treatment compound is 3-methacryloxypropyltrimethoxysilane.

11. The method of claim 7, wherein the treatment compound is 3-methacryloxypropyltrimethoxysilane.

12. The method of claim 8, wherein the treatment compound is 3-methacryloxypropyltrimethoxysilane.

13. The method of claim 2, wherein the treating compound is not reactive with the organosilicon compound.

14. The method of claim 2, wherein the treating compound does not form a solid polymer during said step of exposing the adsorbent to a treating compound.

15. The method of claim 3, wherein the treating compound does not form a solid polymer during said step of exposing the adsorbent to a treating compound.

* * * * *